US009730617B2

(12) United States Patent
Schlumbohm et al.

(10) Patent No.: US 9,730,617 B2
(45) Date of Patent: Aug. 15, 2017

(54) POWER MEASUREMENT METHOD AND APPARATUS

(75) Inventors: Stephan Schlumbohm, Aachen (DE); Heribert Baldus, Aachen (DE); Wiebren Zijlstra, Groningen (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 600 days.

(21) Appl. No.: 13/120,018

(22) PCT Filed: Sep. 17, 2009

(86) PCT No.: PCT/IB2009/054076
§ 371 (c)(1),
(2), (4) Date: Mar. 21, 2011

(87) PCT Pub. No.: WO2010/035187
PCT Pub. Date: Apr. 1, 2010

(65) Prior Publication Data
US 2011/0178760 A1 Jul. 21, 2011

(30) Foreign Application Priority Data
Sep. 23, 2008 (EP) .................... 08164910

(51) Int. Cl.
*A61B 5/11* (2006.01)
*A61B 5/00* (2006.01)

(52) U.S. Cl.
CPC .......... *A61B 5/1117* (2013.01); *A61B 5/6831* (2013.01); *A61B 2562/0219* (2013.01); *A63B 2220/40* (2013.01); *A63B 2220/50* (2013.01)

(58) Field of Classification Search
CPC .................................. A61B 5/1117
USPC .............. 702/141, 33, 57, 142, 150
See application file for complete search history.

(56) References Cited

U.S. PATENT DOCUMENTS

| | | | |
|---|---|---|---|
| 6,971,267 B2 * | 12/2005 | Kawai et al. | 73/379.01 |
| 7,150,048 B2 * | 12/2006 | Buckman | 2/465 |
| 7,423,537 B2 * | 9/2008 | Bonnet et al. | 340/573.1 |
| 7,753,861 B1 * | 7/2010 | Kahn et al. | 600/595 |
| 7,966,146 B2 * | 6/2011 | Shkolnikov | 702/141 |
| 8,092,398 B2 * | 1/2012 | Weinberg et al. | 600/595 |
| 8,206,325 B1 * | 6/2012 | Najafi et al. | 600/595 |

(Continued)

FOREIGN PATENT DOCUMENTS

| | | |
|---|---|---|
| EP | 1195139 A1 | 4/2002 |
| EP | 1415770 A1 | 6/2002 |

(Continued)

OTHER PUBLICATIONS

Winter, D.: "Biomechanics and Motor Control of Human Movement"; John Wiley & Sons, Inc., 1990, pp. 56-57.

(Continued)

*Primary Examiner* — Ricky Ngon

(57) ABSTRACT

The power used by a user in performing the vertical component of a movement is estimated. An accelerometer attached to a user measures the acceleration experienced by the user during movement. A processor configured to receive the measurements of the acceleration from the accelerometer, be attached to the user, estimate the vertical accelerations from the received acceleration measurements, and estimate the power used from the vertical accelerations.

7 Claims, 3 Drawing Sheets

(56) References Cited

U.S. PATENT DOCUMENTS

| | | |
|---|---|---|
| 8,217,795 B2 * | 7/2012 | Carlton-Foss ............. 340/573.1 |
| 2002/0170193 A1 | 11/2002 | Townsend et al. |
| 2004/0112151 A1 | 6/2004 | Maxwell et al. |
| 2005/0021312 A1 | 1/2005 | Tanaka et al. |
| 2006/0265187 A1 * | 11/2006 | Vock et al. .................. 702/182 |
| 2007/0173377 A1 | 7/2007 | Jamsen et al. |
| 2008/0288200 A1 | 11/2008 | Noble |
| 2009/0240461 A1 | 9/2009 | Makino et al. |
| 2010/0145620 A1 * | 6/2010 | Georgi ................. G01P 15/093 702/6 |

FOREIGN PATENT DOCUMENTS

| | | |
|---|---|---|
| GB | 2422790 A | 8/2006 |
| WO | 2007082389 A1 | 7/2007 |
| WO | 2007/105648 A1 | 9/2007 |

OTHER PUBLICATIONS

Aminian et al: "Physical Activity Monitoring Based on Accelerometry:Validation and Comparison With Video Observation"; Medical and Biological Engineering and Computing, May 1999, vol. 37, No. 3, pp. 304-308.

Janssen, et al. "Determinants of the Sit-to-State Movement: A Review", Phys. Ther. 2002; 82:866-879.

O'Sullivan, et al. "Sit to Stand Transfer", Illinois Neurological Institute, Rehabilitation Dept. Physical Therapy, (2007) Physical Rehabilitation 5th Ed. Philadelphia F.A. Davis Co. © 2003-2005 Arena Health Systems Phys-X Ver6.0 Reviewed 2009.

Bhattacharya, "Eight Steps to Improving Sit-to-Stand Transfers" Livestrong.com, Last Updated: Feb. 7, 2014.

* cited by examiner

POWER MEASUREMENT METHOD AND APPARATUS

TECHNICAL FIELD OF THE INVENTION

The invention relates to a method and apparatus for measuring the power or strength used during a movement, and in particular to measuring the power or strength used in the vertical parts of the movement.

BACKGROUND TO THE INVENTION

Falls are one of the greatest health risk factors to elderly people. It has been found that around one third of people above the age of 65 fall at least once a year.

Many of these falls could be avoided by early identification of fall risk and the application of effective and targeted fall prevention programs. Fall prevention trials based on strength and balance training (SBT) have shown that the risk of falling in elderly people can be reduced.

Balance performance measures can be used as early indicators of fall risk and to measure the progress of fall prevention programs. In particular, the Sit-to-Stand (STS) transfer has been identified as an important movement in that respect. Domain experts compare the graph of the power generated during a Sit-To-Stand transfer for fall prevention with the ECG graph in cardiovascular disorders. In daily life, the STS transfer is performed by every person multiple times a day.

Conventionally, only clinical measurement systems (such as those including a force plate and an optical marker system) allow an accurate quantification of power during a sit-to-stand transfer. In these measurement systems, the force plate provides the vertical ground reaction force and the optical marker system provides a measure of displacement in three dimensions. The combination of both measurements is used to quantify the power during a Sit-to-Stand transfer.

These measurement systems have several drawbacks. Firstly, they are clinical equipment, which requires the user to attend a clinic. They are labour intensive to prepare for and perform the measurement (particularly if a number of optical markers need to be attached to specific parts of the body). In addition, they only provide a snapshot of the user's balance performance, where, due to the clinical setting, the user commonly performs beyond average capability. Furthermore, the measurement systems involve a procedure that is quite cumbersome to the user.

There is therefore a need for a method and system for measuring the power used during a vertical movement, such as a sit to stand transfer, that is easy and simple for the user to operate.

SUMMARY OF THE INVENTION

In accordance with a first aspect of the invention, there is provided an apparatus for estimating the power used by a user in performing the vertical component of a movement, the apparatus comprising an accelerometer for attachment to a user and for measuring the acceleration experienced by the user; the apparatus further comprising a processor configured to receive the measurements of the acceleration from the accelerometer attached to the user; estimate the vertical accelerations from the received measurements; and estimate the power used from the vertical accelerations.

In accordance with a second aspect of the invention, there is provided a method for estimating the power used by a user in performing the vertical component of a movement, the method comprising obtaining measurements of the vertical acceleration experienced by the user in performing the movement from an accelerometer attached to the user; and determining an estimate of the power used from the measurements of the vertical acceleration.

In accordance with a third aspect of the invention, there is provided a computer program product, comprising computer program code that, when executed on a computer or processor associated with an accelerometer attached to a user estimates the power used by a user in performing the vertical component of a movement by receiving measurements from the accelerometer; determining the vertical acceleration experienced by the user in performing the movement from the received measurements; and determining an estimate of the power used from the measurements of the vertical acceleration.

BRIEF DESCRIPTION OF THE DRAWINGS

Embodiments of the invention will now be described, by way of example only, with reference to the following drawings, in which.

DETAILED DESCRIPTION OF THE PREFERRED EMBODIMENTS

Figure 1:
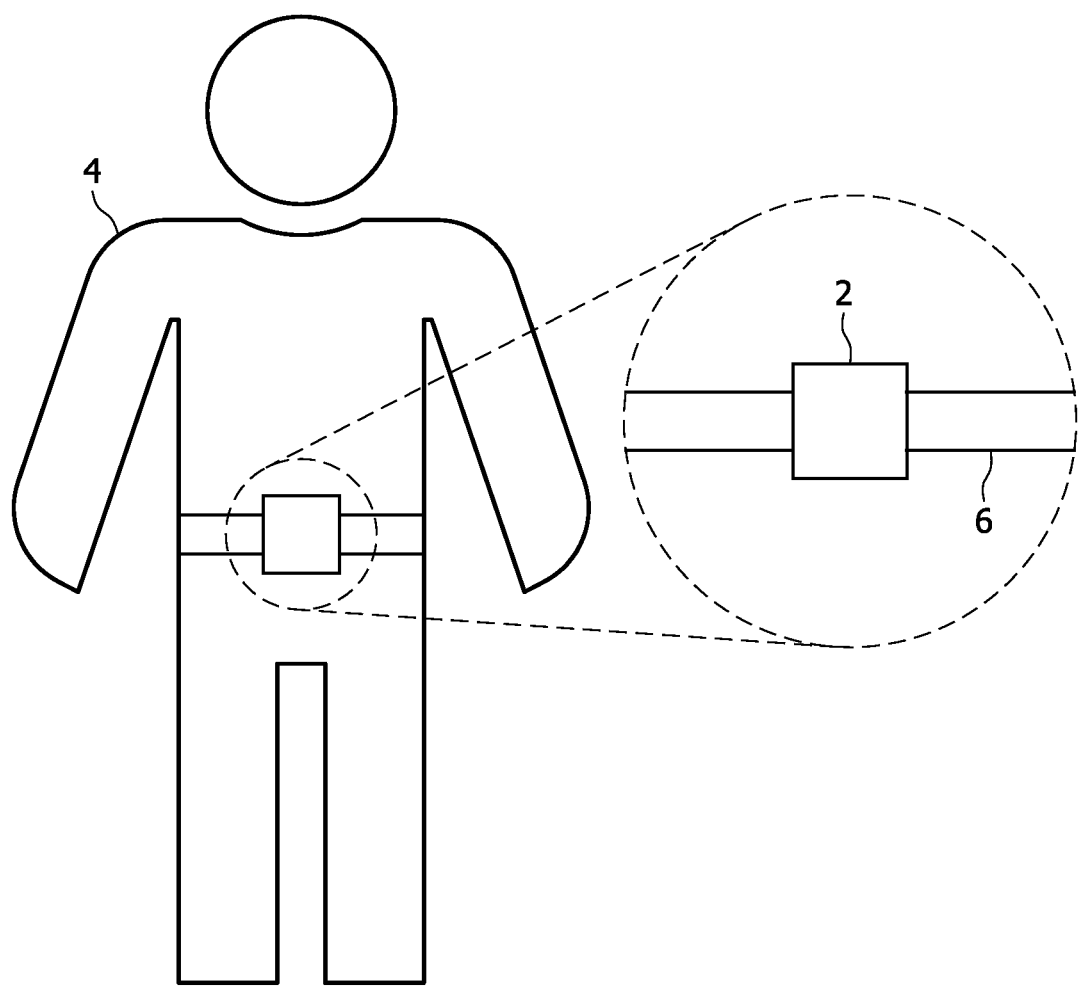
FIG. 1 shows a sensor unit in accordance with the invention attached to a user.

As shown in FIG. 1, the invention provides a sensor unit 2 that is attached to the body of the user 4, preferably the trunk of the body, such as at the pelvis or sternum, by some attachment means 6, such as a belt or strap (or by a neck cord if the unit 2 is in the form of a pendant). The sensor unit 2 is used to determine the power or strength used during a body movement that involves a movement in the vertical direction, such as a sit-to-stand (STS) transfer where the user 4 stands up from a sitting position, from measurements of the acceleration of the body of the user 4.

The sensor unit 2 determines the power or strength used in performing the vertical component of the movement. The sensor unit 2 can calculate the power or strength used over the whole of the vertical movement, but, in alternative embodiments, the sensor unit 2 can be used to determine the power or strength during certain parts of the vertical movement.

Figure 2:
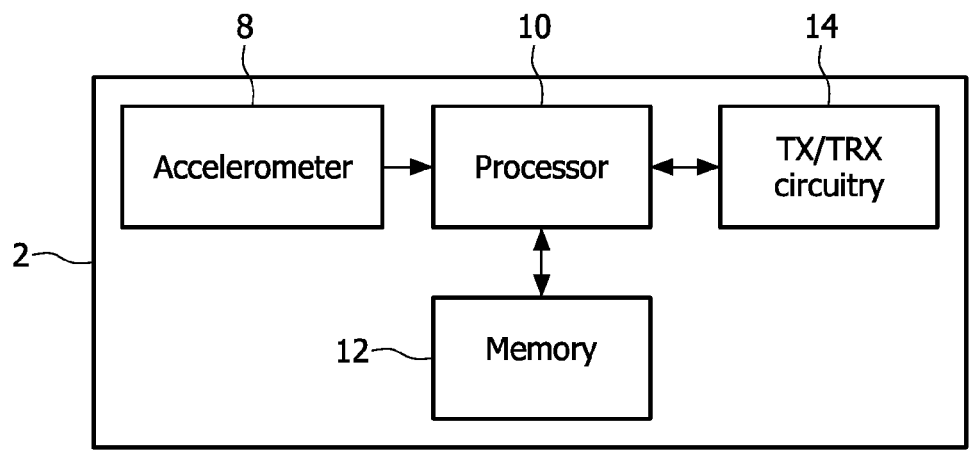
FIG. 2 shows the sensor unit in more detail.

FIG. 2 shows a preferred embodiment of the sensor unit 2 in accordance with the invention. The sensor unit 2 comprises an accelerometer 8 that measures acceleration along three orthogonal axes, and provides corresponding signals. The signals are provided to a processor 10 for analysis. The sensor unit 2 also comprises a memory 12 and transmitter or transceiver circuitry 14. The memory 12 is used for storing measurements from the accelerometer 8, and for storing the results of the analysis by the processor 10. The transmitter or transceiver circuitry 14 is used for transmitting the results of the analysis to a remote unit or a computer where they can be viewed or studied by the user 4 or a healthcare provider.

Preferably, the accelerometer 8 is a micro-electromechanical system (MEMS) accelerometer 8.

In the method for calculating the power or strength used in a movement in a vertical direction described herein, the power or strength is calculated in a fixed reference frame (such as the Earth). As part of this method, it is necessary to determine the vertical acceleration experienced by the user 4 during the vertical movement.

In this embodiment of the invention, the vertical acceleration is calculated just from the measurements of the accelerometer 8 in accordance with the algorithm described below.

In some (less preferred) embodiments, the sensor unit 2 comprises one or more other sensors in addition to the accelerometer 8 for determining the orientation (or changes in the orientation) of the sensor unit 2, such as a gyroscope and/or magnetometer. In this embodiment, it is not necessary to implement the algorithm described below, as the gyroscope and/or magnetometer can provide an indication of the orientation of the sensor unit 2, the measurements from the accelerometer 8 can be converted into the fixed reference frame using the determined orientation and the vertical acceleration can be determined.

Figure 3:
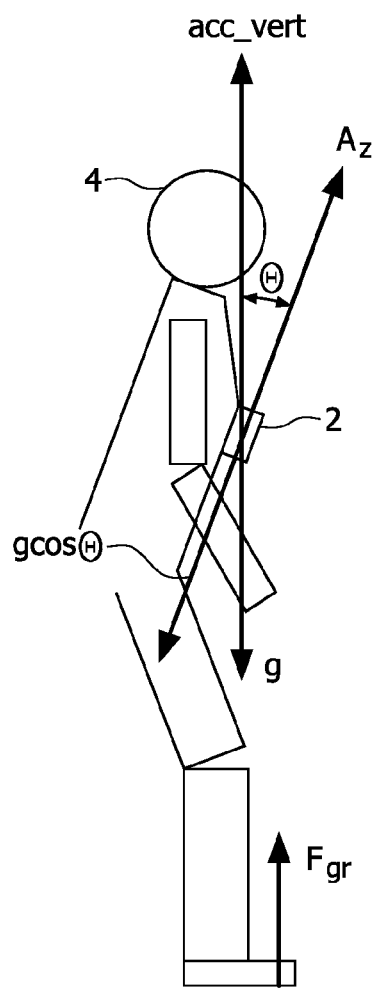
FIG. 3 shows the accelerations and forces acting on the user and exerted by the user in performing a sit to stand transfer.

FIG. 3 shows a side view of the user 4 part way through a movement in a vertical direction, and in particular a sit to stand (STS) transfer. As shown, the sensor unit 2 is attached at the sternum of the user 4.

As the accelerometer 8 is fixed in the sensor unit 2, the orientation of the sensor unit 2 and accelerometer 8 changes during the STS movement, and the sensor unit 2 is shown at an angle $\theta$ from the vertical.

Therefore, to obtain the acceleration in the vertical direction (in the fixed reference frame) it is necessary to compensate the measurements from the accelerometer 8 for these changes in orientation.

Figure 4:
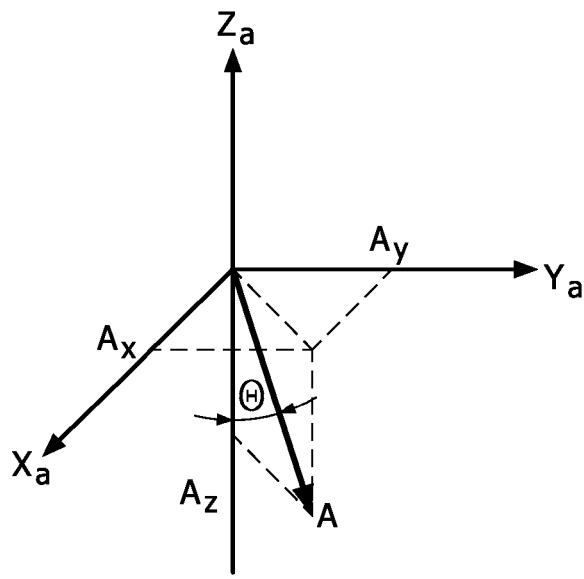
FIG. 4 is a diagram illustrating the calculation of the orientation of an accelerometer from the measured acceleration.

FIG. 4 is an illustration of a measurement of an acceleration A measured by the accelerometer 8. The accelerometer 8 measures the acceleration A acting on it in three dimensions, and provides signals indicating the acceleration A along three orthogonal axes (labelled $x_a$, $y_a$ and $z_a$) to the processor 10.

In this FIG., the acceleration A has components $A_x$, $A_y$ and $A_z$ measured along the three axes respectively.

For an accelerometer 8 that is undergoing small or no accelerations (other than gravity), the acceleration A experienced by the accelerometer 8 will correspond substantially to that of gravity. Thus, from this assumption, it is possible to link the acceleration A to gravity, whose direction is known in the fixed reference frame.

The orientation of the accelerometer 8 can be estimated by calculating the angle between the acceleration A and the axis of the accelerometer 8 that has the highest magnitude of acceleration.

To estimate the orientation of the accelerometer 8, the acceleration acting on the accelerometer 8 is measured, and signals are provided to the processor 10 indicating the components of the acceleration ($A_x$, $A_y$ and $A_z$) along the three orthogonal axes of the accelerometer 8 ($x_a$, $y_a$ and $z_a$ respectively).

The processor 10 calculates the magnitudes of each component of the acceleration A and compares them to identify the component with the highest magnitude.

In the following, the axis ($x_a$, $y_a$ or $z_a$) with the component with the highest magnitude is denoted $z_a'$, and the other two axes are denoted $x_a'$ and $y_a'$. In this way, it is possible for the orientation of the accelerometer 8 to be determined regardless of the initial position of the accelerometer 8. For example, although it may be intended for the $z_a$ axis to correspond to a vertically oriented axis in the fixed reference frame, the accelerometer 8 may not be attached to the user 4 in this way (it may be that the $y_a$ axis corresponds most closely to the vertically oriented axis in the fixed reference frame).

It will be noted that in FIG. 4 the axis with the highest component of acceleration is $z_a$, so this axis is labelled $z_a'$, and the highest component of acceleration is $A_z$.

The processor 10 then determines the angle between the acceleration A and the axis with the highest component of acceleration ($z_a'$). Thus, it can be seen from FIG. 4 that the angle, $\theta$, is given by:

$$\theta = \arctan\left[\frac{\sqrt{A_x^2 + A_y^2}}{A_z}\right] \quad (1)$$

If all components of the acceleration are zero (i.e. $A_x = A_y = A_z = 0$) then $\theta$ and thus the orientation cannot be estimated. In this situation, the accelerometer 8 is in free fall.

Thus, as this angle $\theta$ is determined using gravity as a reference, the angle $\theta$ can be considered as indicating the orientation of the accelerometer 8 and sensor unit 2.

As the accelerometer 8 is free to move with respect to the fixed reference frame, it is desirable to check for local instability caused by rapid changes in the acceleration. In this way, it is possible to compensate for errors in the determined orientation caused by these rapid changes in acceleration. In particular, local instability is checked by the processor 10 computing the variance of the norm of the components of the acceleration A over a period of time.

A number of signals are obtained from the accelerometer 8 representing the acceleration at a number of sampling instants. These sampling instants preferably occur both before and after the sampling instant, i, at which the orientation of the accelerometer 8 is calculated.

The variance of the norm of the components of the acceleration A are calculated using:

$$\text{local\_instability}(i) = \text{var}_{i-b}^{i+a}(\sqrt{A_x(j)^2 + A_y(j)^2 + A_z(j)^2}) > \alpha \quad (2)$$

where a is the number of sampling instants after the sampling instant at which the orientation of the accelerometer 8 is calculated, b is the number of sampling instants before the sampling instant at which the orientation of the accelerometer 8 is calculated and $\alpha$ is a value that indicates a rapid change in acceleration.

The value of $\alpha$ is selected from the range 15-20 m/s², and a and b are in the region of 10.

Once the angle $\theta$ has been calculated, the processor 10 determines the acceleration in a vertical direction relative to the fixed reference frame.

Referring again to FIG. 3, the user 4 is part way through a sit to stand transfer, and the sensor unit 2 and accelerometer 8 is oriented at an angle $\theta$ from the vertical. The axis with the highest component of acceleration ($A_z$) is shown.

The acceleration in the vertical direction is calculated from:

$$\text{acc\_vert} = (A_z - g \cos\theta)\cos\theta + g, \text{ if } \theta > 0 \text{ or there is local instability} \quad (3)$$

$$\text{acc\_vert} = (g \cos\theta - A_z)\cos\theta + g, \text{ if } \theta < 0 \text{ or there is no local instability} \quad (4)$$

where g is the magnitude of the acceleration due to gravity in the vertical direction. It will be appreciated that θ<0 in FIGS. 3 and 4.

Figure 5:
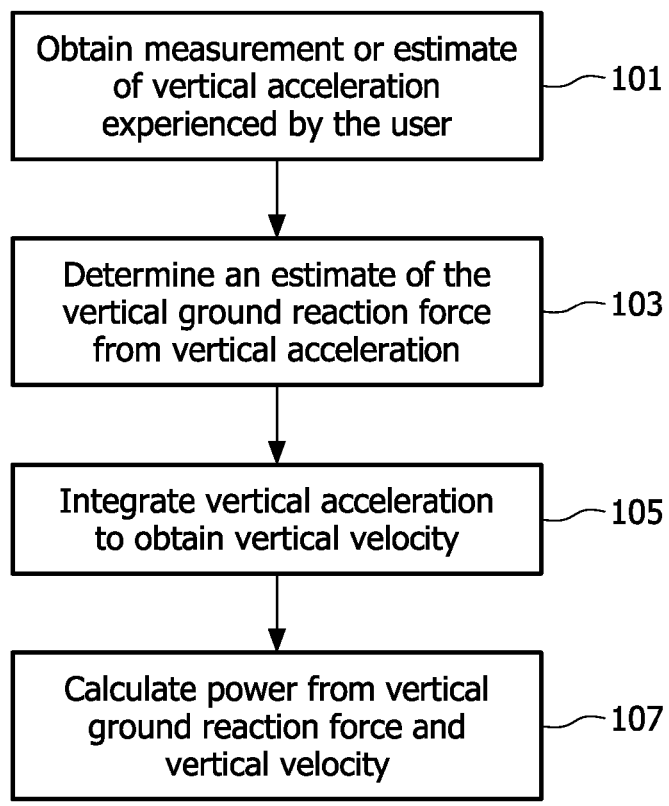
FIG. 5 is a flow chart illustrating the steps in a method according to the invention.

The power or strength used in a movement in the vertical direction can be calculated using the method shown in FIG. 5.

In step 101, a series of measurements or estimates of the acceleration experienced by the user 4 in the vertical direction (in the fixed reference frame) are obtained from the accelerometer 8. As mentioned above, the estimates of the acceleration in the vertical direction can be obtained from a sensor unit 2 whose only sensor is an accelerometer 8, or from a sensor unit 2 that includes an accelerometer, gyroscope and/or magnetometer.

In preferred embodiments, the vertical accelerations can be low pass filtered, for example, by a Butterworth filter with a cut-off frequency of around 2 Hz.

Then, in step 103, the vertical ground reaction force, $F_{gr}$, as a function of time, as shown in FIG. 3, is estimated from $$F_{gr}(t)=(acc\_vert(t)+g)*m \qquad (5)$$

where g is the acceleration due to gravity and m is the mass of the user 4.

Next, in step 105, the series of measurements or estimates of the vertical acceleration are integrated with respect to time to obtain the vertical velocity during the movement. Thus, the vertical velocity, vel_vert(t) is determined from $$vel\_vert(t)=\int (acc\_vert(t))dt \qquad (6)$$

The start and end points of the integration are determined from the measurements from the accelerometer 8. The start point can be identified as the point at which the vertical acceleration starts to vary after a period of time of being in a steady state (for example the vertical acceleration can start to vary from a zero value or from gravity). The end point can be identified as the point at which the vertical acceleration resumes a steady state after a period of movement (for example the vertical acceleration can return to zero or gravity). The processor 10 can determine the start and end points by examining the measurements of the vertical acceleration.

Finally, in step 107, the power used during the vertical movement is calculated using:

$$Power(t)=F_{gr}(t)*vel\_vert(t) \qquad (7)$$

The ground reaction force and power determined from the series of measurements of the vertical acceleration form a time series, which can be plotted as a graph over time. It is then also possible to determine the maximum instantaneous power or maximum loading rate of the power.

It will be appreciated that the only input to the described method is the set of measurements of the vertical acceleration. Thus, instead of separately performing steps 103, 105 and 107, these steps can be combined into a single step in which the power is estimated. In this case, the processor 10 will evaluate:

$$Power(t)=m*(acc\_vert(t)+g)*\int(acc\_vert(t))dt \qquad (8)$$

The method according to the invention can be used in any on-body sensor unit that includes an accelerometer, for example fall detectors and devices for activity monitoring and evaluation, to estimate or determine the power used in a sit-to-stand transfer. This power estimate can provide a physical performance measure for evaluating balance quality and fall risk. In a home health care scenario, this method would enable a home healthcare provider to monitor the users balance quality or risk of falling in an unobtrusive way.

As the power estimation is based on measuring the movement of the centre of mass of the user 4, the accuracy of the power estimation can be improved by placing the sensor unit 2 as close to the centre of mass of the user 4 as possible. For example, the sensor unit 2 is preferably placed close to the pelvis or lower trunk of the user 4.

A further improvement to the power estimation can be obtained by providing accelerometers at two or more parts of the body of the user 4. For example, this can be achieved by providing two sensor units 2, one sensor unit 2 being placed at the sternum, and the other sensor unit 2 being placed at the pelvis. In this embodiment, one of the sensor units 2 will need to receive the measurements from the other sensor unit(s) 2 in order to calculate the power used.

During particular vertical movements, these sensor units 2 will record different accelerations, and so a weighted average of the accelerometer measurements is calculated for use in the power estimation algorithm. Effectively, the weighted average of the accelerations represents the acceleration acting on a virtual centre of mass position in the user 4.

Preferably, this weighted average is given by:

$$a_{centreofmass}=B*a_{pelvis}+C*a_{sternum} \qquad (9)$$

where B and C are constants.

In one embodiment the constants B and C have values of 0.603 and 0.397 respectively, as described in "Biomechanics and Motor Control of Human Movement" by Winter, D. A.

In an alternative embodiment of the invention, instead of processing the acceleration measurements in the processor 10 of the sensor unit 2, the sensor unit 2 or sensor units 2 can measure the acceleration, and transmit these measurements to a separate base unit which performs the necessary calculations to estimate the power used during the movement.

As the sensor unit 2 is small and easy to use, it can be used over a long period of time (relative to the period of time possible in a clinical setting) to quantify the power or strength during a particular type of body movement, such as a sit-to-stand transfer. The power or strength can be measured in an unobtrusive fashion, and the methods described above provide a similar accuracy to clinical measurement systems.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for estimating power used by a user in performing a vertical component of a movement, the apparatus comprising:
   an accelerometer configured for attachment to a user and configured for measuring components of the acceleration along three orthogonal axes experienced by the user;
   a processor configured to:
      receive the measured components of the acceleration $A_x$, $A_y$, and $A_z$, along three orthogonal axes $x_a$, $y_a$, and $z_a$ from the accelerometer,
      estimate an orientation of the accelerometer by calculating an angle θ between the acceleration and an axis that has the component with the highest magnitude of acceleration by:
         calculating the magnitude of each of the components of the acceleration from the measurements indicating the components of the acceleration $A_x$, $A_y$, and $A_z$ along the three orthogonal axes $x_a$, $y_a$, and $z_a$ of the accelerometer,
         identifying the acceleration component with the highest magnitude,
         determining the angle θ between the acceleration and the axis with the highest component of acceleration from $$\theta = \arctan\left[\frac{\sqrt{A_2^2 + A_3^2}}{A_1}\right]$$

where $A_1$ is the component with the highest magnitude, and $A_2$ and $A_3$ are other components of acceleration along the three orthogonal axes;
   estimate a vertical acceleration component from the acceleration components and the angle θ, and
   estimate the power used from the vertical acceleration component; and
   a transceiver configured to receive the estimated power from the processor, and configured to transmit the estimated power to a remote computer.

2. The apparatus as claimed in claim 1, wherein the movement is a sit-to-stand (STS) transfer and the accelerometer is configured for measuring the acceleration along the three orthogonal axes during the STS transfer.

3. The apparatus as claimed in claim 2, wherein the processor is further configured to calculate local instability over j samplings based on a variance of a norm of the components of the acceleration by calculating:

$$\text{var}_{i-b}{}^{i+a}(\sqrt{A_x(j)^2 + A_y(j)^2 + A_z(j)^2})$$

where a is a number of sampling instants after a sampling instant i at which the orientation of the calculator is calculated,
b is a number of sampling instants before the sampling instant i at which the orientation of the calculator is calculated.

4. The apparatus as claimed in claim 3, wherein the processor is configured to indicate instability when $$\text{var}_{i-b}{}^{i+a}(\sqrt{A_x(j)^2 + A_y(j)^2 + A_z(j)^2})$$

is greater than 15 m/s².

5. The apparatus as claimed in claim 1, further comprising:
   a remote display device of the remote computer configured to:
   receive the estimate of power used during the STS transfer from the transceiver, and
   display the estimate of power used during the STS transfer.

6. The apparatus as claimed in claim 1, wherein the processor is further configured to compensate the measured components of acceleration for a change in orientation of the accelerometer.

7. A physical therapy apparatus for estimating power used by a user in performing a sit-to-stand (STS) transfer, the apparatus comprising:
   an accelerometer configured for attachment to a user and configured for measuring acceleration experienced by the user during an STS transfer; and
   a processor configured to:
      receive the measurements of the acceleration from the accelerometer;
      estimate vertical accelerations from the received measurements by:
         estimating an orientation of the accelerometer from the received acceleration measurements; and
         identifying the vertical accelerations in the received acceleration measurements using the estimated orientation; and
   wherein the processor is further configured to:
      based only on the estimated vertical accelerations, a mass of the user, and gravity, estimate the power used during the STS transfer; and
      compensate for errors in the estimated orientation by computing a variance of a norm of components of the received acceleration measurements over a period of time; and
   wherein the apparatus further comprises a transceiver configured to receive the estimated power from the processor, and configured to transmit the estimated power to a remote display device to cause the remote display device to display an indication of an instability when the computed variance is greater than a threshold.

* * * * *